United States Patent
Karvandi

(10) Patent No.: US 10,993,726 B2
(45) Date of Patent: May 4, 2021

(54) BLOOD FLOW RESTRICTION EXERCISE STRAP

(71) Applicant: Orangutan Organization, Inc., Walpole, MA (US)

(72) Inventor: Kusha Karvandi, Leander, TX (US)

(73) Assignee: Orangutan Organization, Inc., Walpole, MA (US)

( * ) Notice: Subject to any disclaimer, the term of this patent is extended or adjusted under 35 U.S.C. 154(b) by 309 days.

(21) Appl. No.: 16/126,330

(22) Filed: Sep. 10, 2018

(65) Prior Publication Data

US 2019/0076153 A1 Mar. 14, 2019

Related U.S. Application Data

(63) Continuation of application No. 29/631,433, filed on Dec. 29, 2017.
(Continued)

(51) Int. Cl.
*A61B 17/132* (2006.01)
*A63B 23/035* (2006.01)
(Continued)

(52) U.S. Cl.
CPC .......... *A61B 17/1327* (2013.01); *A61H 11/00* (2013.01); *A63B 21/00047* (2013.01); *A63B 21/4011* (2015.10); *A63B 21/4017* (2015.10); *A63B 21/4025* (2015.10); *A63B 23/035* (2013.01); *A63B 69/0059* (2013.01); *A63B 71/06* (2013.01); *A44B 11/12* (2013.01);
(Continued)

(58) Field of Classification Search
CPC ..... A44B 11/12; A44B 11/125; A61B 17/132; A61B 17/1322; A61B 17/1327; A61H 11/00; A61H 2011/005; A63B 21/0552; A63B 21/0557; A63B 21/068; A63B 21/1663; Y10T 24/4016
See application file for complete search history.

(56) References Cited

U.S. PATENT DOCUMENTS 40,911 A * 12/1863 Cowles .................. A44B 11/12
24/170
D55,826 S 7/1920 Stih
(Continued)

OTHER PUBLICATIONS

Amazon Occlusion Training Bands, [online], [site visited Feb. 24, 2017]. Available from Internet, URL https://www.amazon.com/dp/B00ZJTEM1U/.
(Continued)

*Primary Examiner* — Ryan J. Severson
(74) *Attorney, Agent, or Firm* — Zeller IP Group, PLLC; Kyle M. Zeller

(57) ABSTRACT

A blood flow restriction (BFR) exercise strap. The strap is configured with a coupling at a first end of an elastic band. A second free end of the band is releasably retained in the coupling by a lever arm that is biased in a closed configuration against a plurality of teeth carried on an interior surface of the base. The band has graduated indicia carried thereon for determining a constriction level applied by the band to a limb of the user. The graduated indicia allow the user to set a desired level of constriction on each of a left limb and a right limb to provide the user to develop bilateral symmetry of targeted muscle groups of the limbs.

8 Claims, 3 Drawing Sheets

Related U.S. Application Data

(60) Provisional application No. 62/555,868, filed on Sep. 8, 2017.

(51) Int. Cl.
*A61H 11/00* (2006.01)
*A63B 21/00* (2006.01)
*A63B 71/06* (2006.01)
*A63B 69/00* (2006.01)
*A61B 90/00* (2016.01)
*A44B 11/12* (2006.01)

(52) U.S. Cl.
CPC . *A61B 2090/0807* (2016.02); *A61H 2011/005* (2013.01); *A63B 2071/0694* (2013.01); *A63B 2208/053* (2013.01); *A63B 2213/006* (2013.01)

(56) References Cited

U.S. PATENT DOCUMENTS

| | | | |
|---|---|---|---|
| 1,447,967 A * | 3/1923 | Rutledge | A44B 11/25 24/311 |
| 1,771,689 A * | 7/1930 | Arthur | A61B 17/1327 606/203 |
| 1,870,052 A * | 8/1932 | Jones | A61B 17/1327 606/203 |
| D92,333 S | 5/1934 | Botty | |
| 2,009,325 A | 7/1935 | Morris | |
| 2,234,961 A * | 3/1941 | Canada | A61B 17/1327 606/203 |
| 2,363,872 A * | 11/1944 | Kiessling | A44B 11/065 24/170 |
| 2,893,394 A | 7/1959 | Wilhelm | |
| 3,042,986 A * | 7/1962 | Racette | A44B 11/12 24/170 |
| 3,083,428 A | 4/1963 | Mcgill | |
| 3,086,529 A | 4/1963 | Munz et al. | |
| 3,100,484 A | 8/1963 | Berl | |
| D215,195 S | 9/1969 | Krengel | |
| 3,641,630 A * | 2/1972 | Farley | B65D 63/16 24/68 CD |
| D242,290 S | 11/1976 | Evans | |
| D243,293 S | 2/1977 | Scheimberg | |
| 4,184,617 A | 1/1980 | Lyon | |
| 4,414,969 A | 11/1983 | Heyman | |
| D281,005 S | 10/1985 | Larsen | |
| 4,733,440 A * | 3/1988 | Ogawa | A44B 11/06 24/170 |
| D300,810 S | 4/1989 | Reaume | |
| 4,881,303 A * | 11/1989 | Martini | A44B 11/14 24/170 |
| D304,977 S | 12/1989 | Pappas | |
| D311,232 S | 10/1990 | Drennan et al. | |
| 5,005,527 A * | 4/1991 | Hatfield | A01K 27/005 119/793 |
| 5,036,864 A * | 8/1991 | Yewer, Jr. | A41F 9/002 128/876 |
| D322,854 S | 12/1991 | Campbell | |
| 5,161,351 A * | 11/1992 | Woodruff | A44B 11/14 24/170 |
| D333,626 S | 3/1993 | Chang | |
| D333,640 S | 3/1993 | Keller | |
| 5,254,065 A | 10/1993 | Pollock | |
| 5,279,057 A | 1/1994 | Melin et al. | |
| 5,291,638 A * | 3/1994 | Huang | A44B 11/14 24/170 |
| D346,482 S | 5/1994 | Merrill | |
| D350,401 S | 9/1994 | Kok | |
| 5,500,959 A | 3/1996 | Yewer, Jr. | |
| D369,674 S | 5/1996 | Schreiner et al. | |
| D373,011 S | 8/1996 | Rippel | |
| D373,803 S | 9/1996 | Winans | |
| 5,551,447 A | 9/1996 | Hoffman et al. | |
| D383,993 S | 9/1997 | Kalbach | |
| 5,661,877 A * | 9/1997 | Bloomer | A44B 11/12 24/170 |
| 5,685,787 A | 11/1997 | Kogut | |
| D389,987 S | 2/1998 | O'Byrne et al. | |
| D390,492 S | 2/1998 | Riley | |
| D393,337 S | 4/1998 | Seki | |
| 5,740,591 A | 4/1998 | Hopkins | |
| 5,745,920 A | 5/1998 | Olivier | |
| 5,746,685 A | 5/1998 | Glaser | |
| D397,838 S | 9/1998 | Waggoner et al. | |
| 5,816,984 A | 10/1998 | Weiss | |
| 5,888,180 A | 3/1999 | Dewberry | |
| 6,049,953 A | 4/2000 | McCay et al. | |
| D427,651 S | 7/2000 | Bodman | |
| 6,081,925 A | 7/2000 | Reiber | |
| D432,446 S | 10/2000 | Santos | |
| D433,227 S | 11/2000 | Evans | |
| 6,149,618 A * | 11/2000 | Sato | A61B 17/1322 602/75 |
| D437,623 S | 2/2001 | Ormsby | |
| D441,413 S | 5/2001 | Cataldi, Jr. et al. | |
| D449,136 S | 10/2001 | Vallance | |
| D453,366 S | 2/2002 | French | |
| 6,349,493 B1 | 2/2002 | Newman et al. | |
| 6,352,074 B1 | 3/2002 | Okada | |
| D455,213 S | 4/2002 | Weaver et al. | |
| D457,688 S | 5/2002 | Cordero | |
| 6,381,810 B2 * | 5/2002 | Hsieh | A44B 11/06 24/170 |
| 6,398,749 B1 | 6/2002 | Slautterback | |
| D462,772 S | 9/2002 | Lamping et al. | |
| 6,485,448 B2 | 11/2002 | Lamping et al. | |
| D470,793 S | 2/2003 | Horn et al. | |
| 6,564,385 B2 | 5/2003 | McCarthy | |
| D481,851 S | 11/2003 | Greaige | |
| D488,287 S | 4/2004 | Berger | |
| D488,288 S | 4/2004 | Eggers | |
| D488,842 S | 4/2004 | Mills et al. | |
| D489,422 S | 5/2004 | Feder | |
| D495,118 S | 8/2004 | Sherman | |
| 6,884,254 B2 * | 4/2005 | Brooks | A61B 17/1327 24/71 R |
| 6,899,720 B1 * | 5/2005 | McMillan | A61B 17/1322 606/203 |
| D508,872 S | 8/2005 | Hoeppner | |
| D511,450 S | 11/2005 | Seth | |
| 6,960,223 B1 * | 11/2005 | Ambach | A61B 17/1327 606/203 |
| 7,043,762 B2 | 5/2006 | Greenhalgh | |
| D529,896 S | 10/2006 | Anderson et al. | |
| D546,953 S | 7/2007 | Young | |
| D547,228 S | 7/2007 | Rozsavolgyi | |
| D558,427 S | 1/2008 | Solin | |
| D558,842 S | 1/2008 | Dore et al. | |
| D562,123 S | 2/2008 | Jackson | |
| 7,334,301 B2 * | 2/2008 | Huang | B60P 7/0823 24/170 |
| 7,444,720 B2 * | 11/2008 | Huang | A44B 11/12 24/170 |
| 7,468,067 B2 * | 12/2008 | Licata | A61B 17/132 24/170 |
| 7,712,192 B2 * | 5/2010 | Lin | A61B 17/132 24/70 ST |
| 7,950,072 B1 | 5/2011 | Hanson | |
| D647,279 S * | 10/2011 | Shi | D2/629 |
| D648,440 S | 11/2011 | Allen | |
| D649,648 S | 11/2011 | Cavalieri et al. | |
| D650,485 S | 12/2011 | Jaccard | |
| D653,408 S | 1/2012 | Sajid | |
| D659,057 S * | 5/2012 | Patton | D12/133 |
| D659,570 S | 5/2012 | Hetke et al. | |
| D662,557 S | 6/2012 | Nawracaj | |
| D676,627 S | 2/2013 | Doss | |
| 8,439,943 B2 * | 5/2013 | Chao | A61B 17/1327 606/203 |
| 8,486,106 B2 * | 7/2013 | Warburton | A61B 17/1322 606/203 |

(56) References Cited

U.S. PATENT DOCUMENTS

| | | | |
|---|---|---|---|
| 8,561,267 B2 * | 10/2013 | Chang | A44B 11/12 24/499 |
| D697,712 S | 1/2014 | Morton | |
| 8,635,746 B2 * | 1/2014 | Bellamy | A61B 17/1327 24/170 |
| 8,747,284 B2 | 6/2014 | Ingram | |
| D707,917 S | 7/2014 | James et al. | |
| D710,739 S | 8/2014 | Miller | |
| D712,555 S | 9/2014 | Berg | |
| 8,821,425 B2 | 9/2014 | Cox | |
| 8,834,331 B1 | 9/2014 | Boatwright | |
| 8,887,313 B2 | 11/2014 | McGuin | |
| D726,841 S | 4/2015 | Wright | |
| D733,525 S | 7/2015 | Petzl | |
| D742,461 S | 11/2015 | Baldwin | |
| D747,176 S | 1/2016 | Petzl | |
| D747,591 S | 1/2016 | Holloway et al. | |
| D749,568 S | 2/2016 | Magi et al. | |
| D750,716 S | 3/2016 | Pouliot | |
| D751,065 S | 3/2016 | Magi | |
| D753,244 S | 4/2016 | Hovey | |
| D753,344 S | 4/2016 | Kantor | |
| D753,892 S | 4/2016 | Hutchinson | |
| 9,339,693 B1 | 5/2016 | Pegram et al. | |
| D759,993 S | 6/2016 | Stinson | |
| D761,924 S | 7/2016 | Sato | |
| 9,380,817 B1 | 7/2016 | Drake | |
| D788,859 S | 6/2017 | Virtusio | |
| D793,671 S | 8/2017 | Grenville | |
| D794,490 S | 8/2017 | Lindgren | |
| D800,991 S | 10/2017 | Gordon | |
| D810,843 S * | 2/2018 | Karvandi | D21/662 |
| D810,962 S | 2/2018 | McGowan et al. | |
| D815,390 S | 4/2018 | Adrianse | |
| D819,218 S | 5/2018 | Inzer | |
| D827,057 S | 8/2018 | Piotrowski et al. | |
| D828,467 S * | 9/2018 | Karvandi | D21/662 |
| D828,688 S | 9/2018 | Hogard et al. | |
| 10,070,701 B1 * | 9/2018 | Liu | A44B 11/125 |
| 10,117,472 B2 | 11/2018 | Robbins | |
| 10,130,162 B2 | 11/2018 | Tang | |
| 10,194,917 B1 * | 2/2019 | Carson | A61B 17/1327 |
| D841,935 S | 3/2019 | Dennard | |
| D843,525 S * | 3/2019 | Karvandi | D21/694 |
| 10,245,460 B2 | 4/2019 | Hetrick et al. | |
| D847,468 S | 5/2019 | Genao | |
| D849,361 S | 5/2019 | Mouquet | |
| D850,546 S | 6/2019 | Reese | |
| D853,501 S * | 7/2019 | Karvandi | D21/662 |
| D856,444 S * | 8/2019 | Karvandi | D21/662 |
| D858,938 S | 9/2019 | He | |
| D868,270 S | 11/2019 | Nadeau | |
| 10,463,905 B1 | 11/2019 | Smith, Jr. | |
| D870,218 S | 12/2019 | Sudell | |
| D872,200 S | 1/2020 | Antezana | |
| 10,568,636 B2 * | 2/2020 | Demas | A61B 17/1322 |
| D877,451 S | 3/2020 | Ardit | |
| 10,583,971 B2 * | 3/2020 | Kruzel | A44B 11/12 |
| D893,830 S | 8/2020 | Scott et al. | |
| 2001/0022013 A1 | 9/2001 | Hsieh | |
| 2002/0107119 A1 | 8/2002 | Porter | |
| 2002/0160891 A1 | 10/2002 | Gallagher | |
| 2003/0019080 A1 * | 1/2003 | Anthony | A44B 11/14 24/68 R |
| 2003/0148861 A1 | 8/2003 | McBride | |
| 2003/0177561 A1 | 9/2003 | Sloot | |
| 2006/0025807 A1 * | 2/2006 | Licata | A61B 17/1327 606/203 |
| 2006/0089668 A1 * | 4/2006 | Warburton | A61B 17/1322 606/203 |
| 2007/0032359 A1 | 2/2007 | Toronto | |
| 2007/0193004 A1 * | 8/2007 | Chou | A44B 11/006 24/170 |
| 2008/0120755 A1 | 5/2008 | Ingram et al. | |
| 2008/0148529 A1 * | 6/2008 | Huang | A44B 11/14 24/170 |
| 2008/0216213 A1 * | 9/2008 | Lin | A61B 17/132 2/338 |
| 2008/0312682 A1 * | 12/2008 | Shams | A61B 17/1327 606/203 |
| 2009/0183299 A1 | 7/2009 | Conway | |
| 2010/0217307 A1 * | 8/2010 | Warburton | A61B 17/132 606/203 |
| 2010/0312271 A1 * | 12/2010 | Chao | A61B 17/1327 606/203 |
| 2011/0125036 A1 * | 5/2011 | Nakajima | A61F 5/34 600/500 |
| 2011/0247179 A1 * | 10/2011 | Bellamy | A61B 17/1327 24/19 |
| 2011/0313435 A1 * | 12/2011 | Aldridge | A61B 17/823 606/151 |
| 2013/0331236 A1 | 12/2013 | Moss | |
| 2014/0213420 A1 | 7/2014 | Harris | |
| 2015/0052655 A1 | 2/2015 | McCully | |
| 2015/0158615 A1 * | 6/2015 | Downs | B65F 1/06 24/71 ST |
| 2016/0174665 A1 * | 6/2016 | Kung | A44B 11/12 24/170 |
| 2016/0317864 A1 * | 11/2016 | Sato | A63B 23/12 |
| 2017/0000249 A1 | 1/2017 | Beck | |
| 2017/0274236 A1 | 9/2017 | Farias | |
| 2017/0354422 A1 * | 12/2017 | Brub | A61B 17/1327 |
| 2018/0020781 A1 | 1/2018 | McNeill | |
| 2018/0042616 A1 * | 2/2018 | Demas | A61B 17/1322 |
| 2018/0140929 A1 | 5/2018 | Pellegrino | |
| 2018/0154818 A1 | 6/2018 | Sauerwald | |
| 2018/0273263 A1 * | 9/2018 | Kruzel | A44B 11/12 |
| 2019/0060700 A1 | 2/2019 | Abecasis | |
| 2019/0076153 A1 * | 3/2019 | Karvandi | A61H 11/00 |
| 2019/0274693 A1 * | 9/2019 | Carson | A61B 17/1327 |
| 2019/0314036 A1 * | 10/2019 | Huang | F16B 2/04 |
| 2020/0171342 A1 | 6/2020 | Peery | |

OTHER PUBLICATIONS

Amazon, "Occlusion Training Bands", Feb. 3, 2018. https://www.amazon.com/Occlusion-Training-Bands-BFR-Restriction/dp/B0777QRRH H?ref_=ast_sto_dp. Shown on p. 1. (Year: 2018).

Amazon, "BFR Training Bands", Jul. 27, 2018. https://www.amazon.com/BFR-BANDS-Occlusion-Restriction-Quick-Release/dp/B07D9V4TWJ/ref=cm_cr _arp_d_product_top?ie=UTF8. Shown on p. 1. (Year: 2018).

Bear Grips by Bear Grips dated Jan. 3, 2015. Found online [Dec. 6, 2018]. https://www.amazon.com/Bear-Grips-II-band-support-lifting/dp/B00OPW9W3U/ref =cm_erarp _d_prod uct_top?ie=UTF8.

BFR Bands by BFR Bands dated Oct. 31, 2015. Found online [Dec. 6, 2018]. https ://www.amazon.com/BFR-Occlusion-Training-Restriction-Quick-Release/dp/B01C2 BAE82/ref=cm_cr _arp _d_prod-uct_top?ie=UTF8.

BFR Bands, [online], [site visited Jan. 25, 2017]. Available from Internet, URL: http://www.bfrbands.com/.

Elite 2.0 BFR Bands, [online], [site visited Jan. 25, 2017]. Available from Internet, URL:http://www.occlusiontrainingbands.com/product/elite-bfr-bands/.

Facebook Exerscribe Photos, Mar. 11, 2017, [online], [site visited Jul. 17, 2020]. Retrieved from url:https://www.facebook.com/exerscribe/photos/a.478392955590457/1250285948401150/ (Year: 2017).

Occlusion Training Bands by Exerscribe dated Mar. 5, 2015. Found online [Dec. 6, 2018]. https://www.amazon.com/Occlusion-Training-Restriction-without-Lifting/product-reviews/BOOZHJ8DYE/ref=cm_er getr_d_paging_btm_8?ie=UTF8&reviewerType=all_reviews&sortBy=recent&pageNumber=8.

Quad by BFR dated no date given. Found online [Dec. 6, 2018]. https://www.bfrshop.com/collections/lower-body-bands/products/quad-wrap-occlusion-training-bands.

QUAD Wraps by BFR Bands dated Oct. 13, 2017. Found online [Dec. 6, 2018]. https://www.youtube.com/watch?time_continue=48&v=vQ6aKq08taA.

(56) References Cited

OTHER PUBLICATIONS

Youtube PRO Premium BFR Bands Trailer, Oct. 21, 2019, [online], [site visited Jul. 17, 2020]. Retrieved from url: https://www.youtube.com/watch?v=AspbWrkLey8&feature=emb_logo (Year: 2019).

Youtube Pro X and Pro BFR Bands Comparison, Oct. 20, 2017, [online], [site visited Jul. 17, 2020]. Retrieved from url:https://www.youtube.com/watch?v=ZhoF-Vwrs-A (Year: 2017).

Youtube, "BFR Bands Rigid Edition Arm Bands", Apr. 29, 2020. https://www.youtube.com/watch?v=1aPar6efLc4. Shown at the 0:07 minute mark. (Year: 2020).

\* cited by examiner

BLOOD FLOW RESTRICTION EXERCISE STRAP

CROSS-REFERENCE TO RELATED APPLICATION

This application claims the benefit of priority of U.S. provisional application No. 62/555,868, filed Sep. 8, 2017, the contents of which are herein incorporated by reference. This application is also a continuation of U.S. Design application Ser. No. 29/631,433, filed Dec. 29, 2017, the contents of which are herein incorporated by reference.

BACKGROUND OF THE INVENTION

The present invention relates to exercise equipment, and more particularly to equipment for blood flow restriction exercise regimens.

Blood flow restriction (BFR) exercise regimens involve a band that is tightened around a limb to at least partially occlude the blood flow to a targeted muscle group. They are a form of exercises intended to sculpt the targeted muscle groups.

Existing BFR straps are difficult for the user to apply to obtain an even constriction between their limbs to achieve the desired bilateral symmetry in the development of the targeted muscle groups. While the BFR straps are fairly easy for the user to apply to their legs, existing BFR straps are difficult to apply by the user in a single handed operation. Likewise, the BFR straps are difficult to remove in a single handed operation when the user has completed an exercise.

As can be seen, there is a need for an apparatus and method for BFR exercise regimens.

SUMMARY OF THE INVENTION

In one aspect of the present invention, a blood flow restriction (BFR) exercise strap is disclosed. The BFR exercise strap includes a coupling having a base and a left and a right sidewall extending upwardly from opposite sides of the base. A slot is laterally disposed at an interior end of the base between the left and the right sidewall. A lever arm is pivotally disposed between the left and the right sidewall. A resilient elastic band has a first end and a second end. A first end is attached to the coupling via the slot and the second end is adapted to be received through an exterior end of the coupling and be secured by the lever arm.

In some embodiments, a torsion spring is configured to bias the lever arm in a closed position. A plurality of teeth may be defined in the base at an intermediate portion thereof, such that the lever arm is configured to urge the band against the plurality of teeth to retain the band within the coupling.

A journaled hole may be defined at an intermediate portion of the left and the right sidewall. A barrel at an end of the lever arm has a pivot pin that protrudes from a left and a right end of the barrel. The pivot pin is received in the journaled hole.

In some embodiments, a pin extends inwardly from at least one of the left and the right sidewall. A first arm of the torsion spring is urged in abutment with the pin and a second arm of the torsion spring urged in abutment with a juncture of the at least one of the left and the right sidewall and the base. A loop of the torsion spring may be carried on the pivot pin.

In preferred embodiments of the invention, graduated indicia are carried on at least one surface of the band. The graduated indicia provide a visual reference of a constriction of the band when applied to a limb of a user.

A patch of a hook material may be applied to the second end of the band and a corresponding patch of pile material may be applied to an intermediate portion of the band.

In other aspects of the invention, a coupling for a blood flow restriction (BFR) exercise strap is disclosed. The coupling includes a base with a left and a right sidewall extend upwardly from opposed sides of the base. A slot may be defined across an interior end of the base between the left and the right sidewall. A plurality of teeth are disposed on an intermediate portion of the base between the left and the right sidewall. A lever arm is pivotally disposed between the left and the right sidewall. A torsion spring biases the lever arm in a closed position against the base.

In some embodiments, a pin extends inwardly from at least one of the left and the right sidewall. A first arm of the torsion spring is urged in abutment with the pin, while a second arm of the torsion spring urged in abutment with a juncture of the at least one of the left and the right sidewall and the base.

A journaled hole may be defined at an intermediate portion of the left and the right sidewall. A barrel at an end of the lever arm having a pivot pin protruding from a left and a right end of the barrel, wherein the pivot pin is received in the journaled hole. A loop of the torsion spring may be carried on the pivot pin.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention an elastic strap and a coupling to allow an user to readily apply and release a strap to their limbs when conducting blood flow restriction (BFR) exercise regimens.

Figure 1:
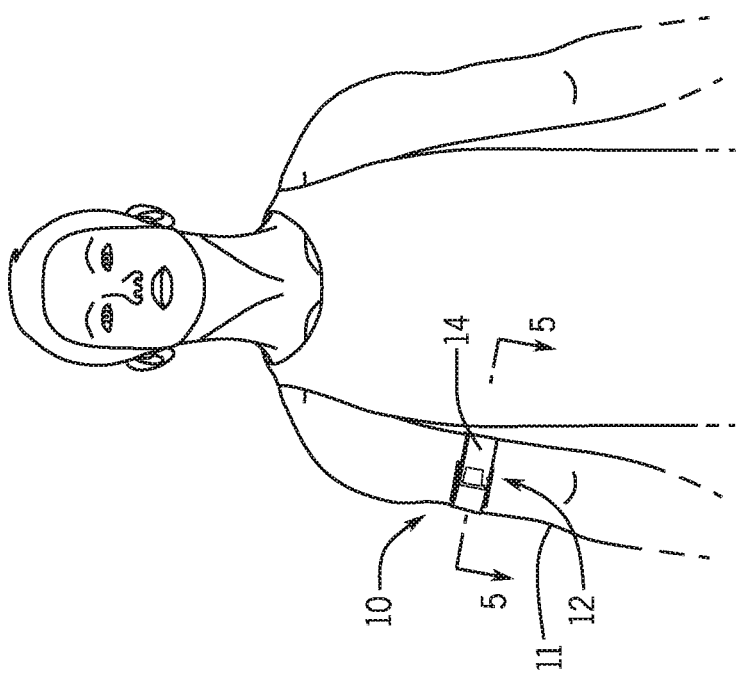
FIG. 1 is a perspective view of the invention in use.

As seen in reference to FIG. 1, a BFR strap 10 is applied to the wearer's limbs to at least partially occlude blood flow to the limb while exercising. The BFR strap includes a band 14 formed of a resilient elastic material having a length to circumscribe a selected location on a wearer's limbs 11, such as the biceps and triceps of the upper arm, muscle groups of the upper legs, or even the lower legs.

Figure 2:
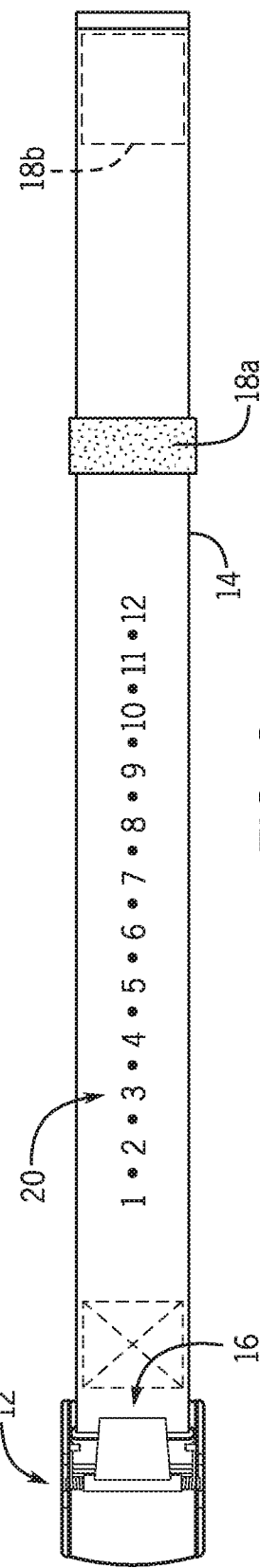
FIG. 2 is a plan view of the strap and buckle of the invention.

As seen in reference to FIG. 2, the BFR strap 10 has a first end with a coupling 12 attached, such as via a stitch, to secure the coupling to the band 14. The strap 10 has a second, free end that is routed through the coupling 12 to secure the strap 10 about the user's limb 11.

The BFR strap 10 may also include a hook and pile fastener 18 to secure the free end of the band 14 when applied to the user's limb 11. A patch of a loop material 18a may be positioned along the band 14 intermediate the first end and the second end. A cooperating patch of hook material 18b may be applied to the free end of the band 14.

At least an exterior surface of the band 14 may carry graduated indicia 20 designating a tightness or constriction level of the BFR strap 10 when it is applied to the user's limb 11. For BFR training regimens, it is desirable to obtain bilateral symmetry in the development of the targeted muscle groups. With the graduated indicia 20, the user can ensure that an even constriction level is achieved between a left limb 11 and a right limb.

Figure 3:
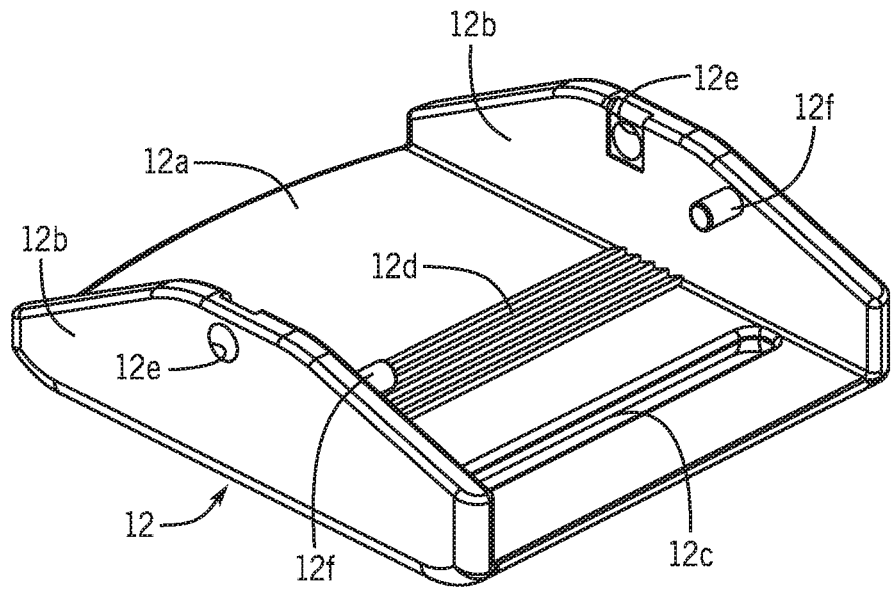
FIG. 3 is a perspective view of the base unit of the invention.
Figure 4:
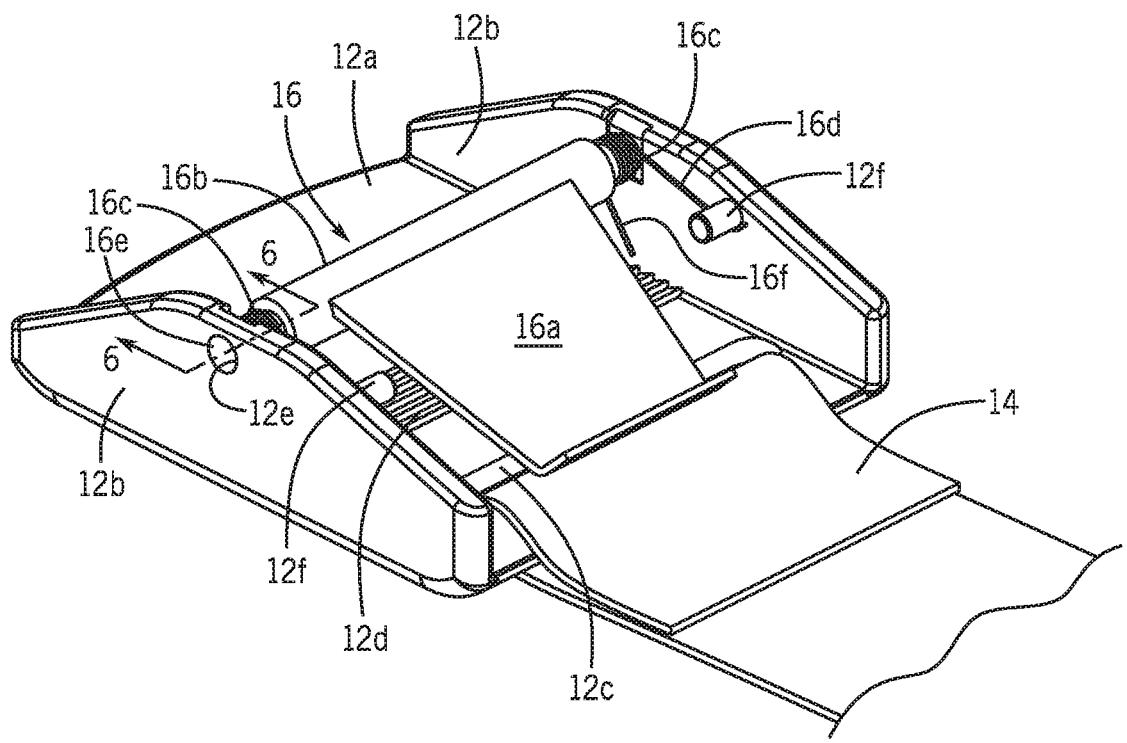
FIG. 4 is a perspective view of the buckle unit of the invention.
Figure 5:
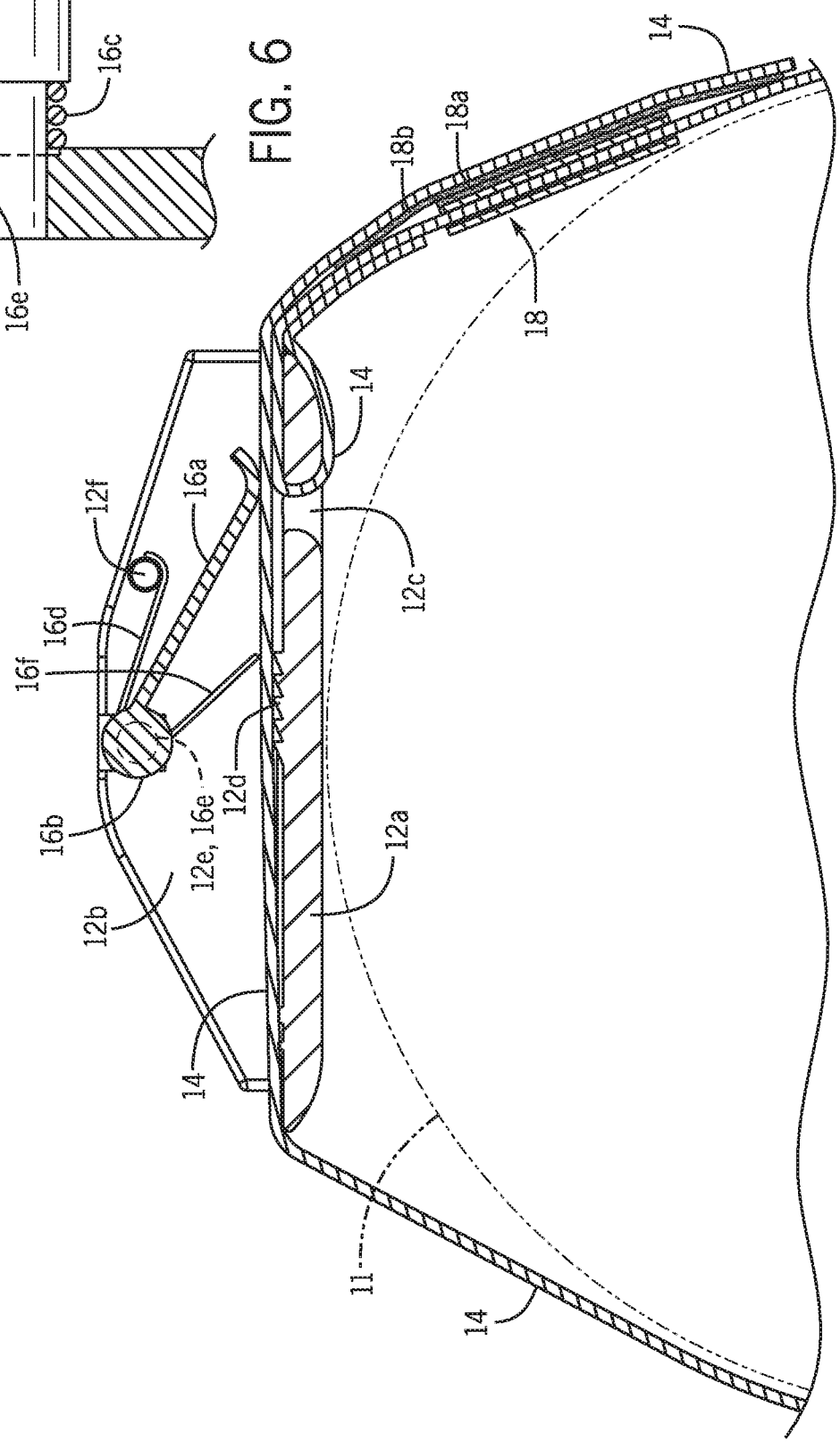
FIG. 5 is a cross-sectional view taken on line 5-5 of FIG. 1.

As seen in reference to FIGS. 3-5, the coupling 12 includes a base 12a formed as a substantially flat plate. A left and a right sidewall 12b protrude upwardly from the base 12a. A slot 12c is defined at an inner end of the base 12a interposed between the left and the right sidewall 12b. A plurality of teeth, or ridges 12d protrude along an intermediate portion of the base 12a between the left and right sidewalls 12b. A journal hole 12e is defined at an upper end of the left and the right sidewalls 12b at an intermediate portion thereof. The journaled holes 12e are dimensioned to pivotally attach a lever 16 to the coupling 12. A stop 12f, or pin, protrudes inwardly along an upper edge of at least one of the left and the right sidewalls 12b.

Figure 6:
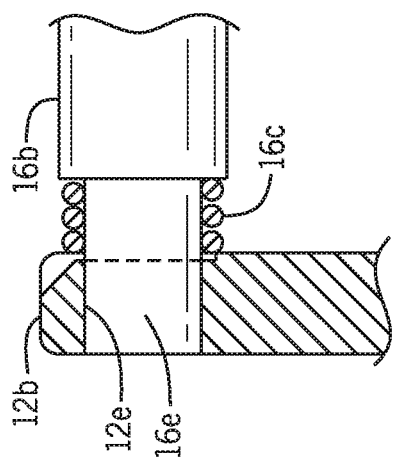
FIG. 6 is a cross-sectional view taken on line 6-6 of FIG. 4.

The lever 16 may include a lever arm 16a extending from a lever barrel 16b. The lever 16 is biased in a closed, strap engaging position via a torsion spring 16c. As best seen in reference to FIGS. 5 and 6, a first leg 16d of the torsion spring 16c has a length to engage with the pin 12f. A loop of the torsion spring 16c may be carried by a pivot shaft 16e extending from the ends of the barrel 16b. The pivot shaft 16e is received in the journaled holes 12e. A second leg 16f of the torsion spring 16c is retained along the junction of the base 12a and one of the left or the right sidewalls 12b.

As best seen in reference to FIG. 4, the first end of the band 14 is received through the slot 12c and may be formed in a loop and secured to an inner portion of the band 14 via a stitch.

Referring again to FIG. 5, in use the band 14 is routed through the coupling 16 by passing the free end of the band 14 through an outer end of the coupling 16 and between the base 12a, the left and the right sidewalls 12b, and beneath the barrel 16b and lever arm 16a. As indicated, the torsion spring 16c biases the lever arm 16 to the closed position to urge the band 14 against the teeth 12d.

The BFR strap 10 may initially be formed in a loop and positioned at the desired location to encircle the user's limb 11. Once positioned, the user may pull on the free end of the band 14 to cinch the loop about the user's limb 11. When the user obtains the desired constriction, they would note the mark of the graduated indicia 20 at the interior end of the coupling 16 so that they can apply the BFR strap 10 to their other limb 11 to the desired tightness. The patch 18b may then be secured to the pile portion 18a to secure the free end of the band 14.

To release the BFR strap 10 the user simply releases the patch 18b from the pile portion 18a and lifts the band 14 so that the lever arm 16a is urged upwardly. The elasticity of the band 14 allows the user to release the tension of the band 14 and allow the band 14 to be retracted through the coupling 16. As will be appreciated from the foregoing disclosure, the BFR strap 10 of the present invention allows for single handed operation for application and removal of the BFR strap 10, while providing graduated indicia for obtaining a desired constriction, providing better symmetry in the development of the targeted muscle groups.

It should be understood, of course, that the foregoing relates to exemplary embodiments of the invention and that modifications may be made without departing from the spirit and scope of the invention as set forth in the following claims.

What is claimed is:

1. A blood flow restriction ("BFR") exercise strap, comprising:
   a coupling comprising:
      a base;
      a left and a right sidewall extending upwardly from opposite sides of the base and comprising a journaled hole defined at an intermediate portion thereof;
      a slot laterally disposed at an interior end of the base between the left and the right sidewall;
      a stop extending inwardly from at least one of the left and the right sidewall;
      a torsion spring comprising:
         a first arm urged in abutment with the stop; and
         a second arm urged in abutment with a juncture of the at least one of the left and the right sidewall and the base; and
      a lever pivotally disposed between the left and the right sidewall, the lever comprising:
         a barrel having a pivot pin protruding from a left and a right end thereof, the pivot pin received in the journaled hole of the left and the right sidewall; and
         a lever arm extending from the barrel, the lever arm biased to a closed position via the torsion spring; and
   a resilient elastic band having a first end and a second end, wherein the first end is attached to the coupling via the slot and the second end is adapted to be received through an exterior end of the coupling and to be secured by the lever arm.

2. The BFR exercise strap of claim 1, further comprising:
   a plurality of teeth defined in the base at an intermediate portion thereof,
   wherein the lever arm is configured to urge the band against the plurality of teeth to retain the band within the coupling.

3. The BFR exercise strap of claim 1, wherein a loop of the torsion spring is carried on the pivot pin.

4. The BFR exercise strap of claim 1, further comprising:
   graduated indicia carried on at least one surface of the band, the graduated indicia providing a visual reference of a constriction of the band when applied to a limb of a user.

5. The BFR exercise strap of claim 4, further comprising:
   a patch of hook material applied to the second end of the band; and
   a corresponding patch of pile material applied to an intermediate portion of the band.

6. A coupling for a blood flow restriction ("BFR") exercise strap, comprising:
   a base;
   a left and a right sidewall extending upwardly from opposed sides of the base;

a slot defined across an interior end of the base between the left and the right sidewall;
a stop extending inwardly from at least one of the left and the right sidewall;
a plurality of teeth disposed on an intermediate portion of the base between the left and the right sidewall;
a lever arm pivotally disposed between the left and the right sidewall; and
a torsion spring to bias the lever arm in a closed position against the base, the torsion spring red in abutment with the stop and a second arm urged in abutment with a juncture of the at least one of the left and the right sidewall and the base.

7. The coupling of claim 6, further comprising:
a journaled hole defined at an intermediate portion of the left and the right sidewall; and
a barrel at an end of the lever arm having a pivot pin protruding from a left and a right end of the barrel, wherein the pivot pin is received in the journaled hole.

8. The coupling of claim 7, wherein a loop of the torsion spring is carried on the pivot pin.

* * * * *